United States Patent [19]

Jones, Jr. et al.

[11] 4,309,426
[45] Jan. 5, 1982

[54] MUSCLE-RELAXANT 1,3,4-THIADIAZIN-2-AMINES

[75] Inventors: Winton D. Jones, Jr., Cincinnati; Francis P. Miller, Loveland, both of Ohio

[73] Assignee: Richardson-Merrell Inc., Wilton, Conn.

[21] Appl. No.: 208,728

[22] Filed: Nov. 20, 1980

Related U.S. Application Data

[63] Continuation-in-part of Ser. No. 71,966, Sep. 4, 1979.

[51] Int. Cl.³ ............................................. A61K 31/54
[52] U.S. Cl. .......................................... 424/246; 544/8
[58] Field of Search ........................................ 424/246

[56] References Cited

PUBLICATIONS

Yoshida et al., *Chemical Abstracts*, vol. 82, entries 57744t, 171096h, 171095g, 170912j, (1975).
Beyer et al., *Justus Liebigs Ann. Chem.*, vol. 741, pp. 45–54 (1970).
Pfeiffer et al., *Z. Chem.*, vol. 17(6), pp. 218–220 (1977).

*Primary Examiner*—John M. Ford
*Attorney, Agent, or Firm*—John J. Kalano; Raymond A. McDonald; William J. Stein

[57] ABSTRACT

A method of achieving a muscle-relaxing effect in a patient comprises administering to a patient in which a muscle relaxing effect is desired an amount effective to achieve a muscle-relaxing effect of a compound of the formula

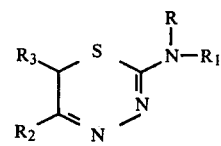

wherein R is H, or $C_{1-7}$ straight or branched chain alkyl;

$R_1$ is H, $C_{1-7}$ straight or branched chain alkyl, allyl or phenyl;

$R_2$ is phenyl, phenyl monosubstituted with F, Cl, $C_{1-4}$ straight or branched chain alkyl or phenyl disubstituted in the 2- and 4-positions with Cl or $C_{1-4}$ straight or branched chain alkyl; and $R_3$ is H or $C_{1-4}$ straight or branched chain alkyl, with the proviso that when $R_3$ is straight or branched chain alkyl, $R_2$ is unsubstituted phenyl;

or a pharmaceutically acceptable acid addition salt thereof.

8 Claims, No Drawings

MUSCLE-RELAXANT 1,3,4-THIADIAZIN-2-AMINES

RELATIONSHIP TO OTHER APPLICATIONS

The present application is a continuation-in-part of application Ser. No. 71,966, filed Sept. 4, 1979 and related to copending applications Ser. Nos. 71,954, 71,952, 71,970 and 72,973 all filed Sept. 4, 1979.

BACKGROUND OF THE INVENTION

The present invention relates to 5-(optionally substituted phenyl)-6$\underline{H}$-1,3,4-thiadiazin-2-amines, having activity as muscle relaxants.

As a general class, 5-(optionally substituted phenyl)-6$\underline{H}$-1,3,4-thiadiazine-2-amines are known as chemical intermediates. See, for example, Japanese Pat. Nos. 74-110,696, 74-110,697 and 74-100,080. Many individual species within the scope of the compounds defined herein and also species related thereto are also known as chemical intermediates. See, for example:

1. Japanese Pat. No. 75 37651;
2. McLean et al., J. Chem. Soc. 1937, 556-9;
3. Avramovici, Analele stiint. univ. "Al. I. Cuza" Iasi, Sect. 1 (Mat. Fiz., chim.). (N.S.) 1, 315-319 (1955). CA51:10541;
4. Beyer et al., Justus Liebigs Ann. Chem. 741, 45-54 (1970);
5. Japanese Pat. No. 74-110,696;
6. Japanese Pat. No. 74-110,697;
7. Bose, Quart. J. Indian Chem. Soc. 1, 51-62 (1924),
8. Beyer et al., Chem. Ber. 89, 107-14 (1956);
9. Japanese Pat. No. 74-88889;
10. Japanese Pat. No. 74-100,080;
11. Bose, Quart. J. Ind. Chem. Soc. 2, 95-114 (1925);
12. Bose et al., J. Indian Chem. Soc. 7, 733-9 (1930);
13. Bulka et al., Z. Chem. 15(12), 482 (1965);
14. Schmidt et al., Tetrahedron Lett. 1975 (1), 33-6;
15. Beyer, Quart, Rep. Sulfur Chem. 5(3), 177-89 (1970);
16. Saraswathi et al., Indian J. Chem. 10(12), 1151-4 (1972);
17. Hampel, Z. Chem. 9(2), 61-2 (1969);
18. Pfeiffer et al., Z. Chem. 17(6), 218-20 (1977);
19. Pfeiffer et al., Synthesis 1977(7), 485-6; and
20. Pfeiffer et al., Synthesis 1977(3), 196-8. Certain species are further known as flame retardants (Japanese Pat. No. 74-5439).

Moreover, some 2-amino-1,3,4-thiadiazines are generally known to have antiviral, anti-inflamatory and analgesic activity (Japanese Pat. No. 74-88889). Additionally, many individual species within the scope of those defined herein, as well as others related in structure are disclosed in this same reference. Some species have been found ineffective as vitamin B substitutes (Robbins et al., Proc. Natl. Acad. Sci. U.S. 24, 141-5 (1938) and anti-tubercular agents (Ban., J. Pharm. Soc. Japan 73, 533-7 (1953) and Bilinski et al., Bull. Acad. Polon, Sci., Ser. Sci. Chim. 13(6), 393-6 (1965)).

Other compounds having significantly different structures are also known to possess pharmacological activity.

4-Methyl-4$\underline{H}$-5,6-dihydro-1,3,4-thiadiazin-2-amines are known to be CNS active (U.S. Pat. No. 3,428,631 and Trepanier et al., J. Med. Chem. 10(6), 1085-7 (1967)). Additionally, 3-substituted-1,2-dihydro-1,3,4-thiadiazin-2-imines are known as slow cure accelerators for rubber (U.S. Pat. No. 2,871,237).

The 5-membered ring-containing 2-amino-1,3,4-thiadiazoles are known to possess CNS depressant activity (Maffii et al., Il Farmaco (Pavia) Ed. Sci. 13, 187-217 (1958); Great Britain Pat. No. 815,188; West German Pat. No. 2,212,245 (or Great Britain Pat. No. 1,380,136); U.S. Pat. No. 3,965,110; U.S. Pat. No. 4,054,665; U.S. Pat. No. 3,919,428; and U.S. Pat. No. 3,992,396) and antihypertensive activity (U.S. Pat. No. 3,746,716).

These 5-membered ring-containing 1,3,4-thiadiazole-2-amines are a class of compounds treated by the prior art as distinct from the 6-membered ring-containing 1,3,4-thiadiazin-2-amines. However, the preparation of both types of compounds are reported together by Rao, Khim. Geterotsikl. Soedin. 1977(3), 291-310, as does Klosa, Arch. Pharm. 287, 12-14 (1954). In the latter reference, the compounds are reported as potential, but untested, tuberculostatics. Compounds of both types are also disclosed in Japanese Pat. No. 74 5439 as fire retardants.

SUMMARY OF THE INVENTION

A method of achieving a muscle-relaxing effect in a patient comprises administering to a patient in which a muscle relaxing effect is desired an amount effective to achieve a muscle-relaxing effect of a compound of the formula

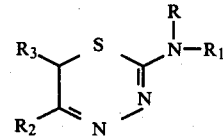

wherein R is H, $C_{1-7}$ straight or branched chain alkyl;

$R_1$ is H, $C_{1-7}$ straight or branched chain alkyl, allyl or phenyl;

$R_2$ is phenyl, phenyl monosubstituted with F, Cl, $C_{1-4}$ straight or branched chain alkyl or phenyl disubstituted in the 2- and 4-positions with Cl or $C_{1-4}$ straight or branched chain alkyl; and $R_3$ is H or $C_{1-4}$ straight or branched chain alkyl, with the proviso that when $R_3$ is straight or branched chain alkyl, $R_2$ is unsubstituted phenyl;

or a pharmaceutically acceptable acid addition salt thereof.

Particularly preferred as muscle relaxants are the fluorophenyl compounds having the following structural formula

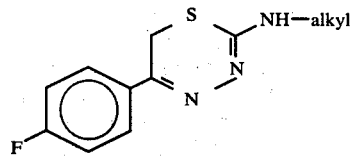

wherein the alkyl group contains 1-7 carbon atoms and is straight or branched chain. Such compounds show a particularly desirable separation of effects producing a muscle relaxant effect at doses which are not sedative. Such fluorophenyl compounds have not been previously described in the literature.

DETAILED DESCRIPTION OF THE INVENTION

Illustrative examples of straight or branched chain $C_{1-7}$ alkyl groups which R and $R_1$ may represent as used herein include, for example, methyl, ethyl, n-propyl, isopropyl, n-butyl, sec-butyl, isobutyl, tert-butyl, n-pentyl, isopentyl, neopentyl, n-hexyl, iso-hexyl, n-heptyl, iso-heptyl, etc. Illustrative examples of straight or branched chain $C_{1-5}$ alkyl and $C_{1-4}$ alkyl groups mentioned in describing the groups $R_1$ and $R_2$-$R_3$, respectively, include, for example, the corresponding examples mentioned above.

Pharmaceutically acceptable acid addition salts of the compounds of Formula I include those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic and 2-phenoxybenzoic, or sulfonic acids such as, for example, methanesulfonic and 2-hydroxyethane sulfonic acid.

Of the compounds of Formula I, those wherein $R_2$ is substituted phenyl are preferred, especially 4-fluorophenyl, and $R_3$ is H.

Illustrative examples of compounds of this invention include those wherein R and $R_1$ are H, $CH_3$, $C_2H_5$ or $C_3H_7$, especially those wherein one of R and $R_1$ is H. These include, for example, N-methyl-5-phenyl-6H-1,3,4-thiadiazin-2-amine, N-ethyl-5-(4-fluorophenyl)-6H-1,3,4-thiadiazin-2-amine, 5-(2,4-dichlorophenyl)-6H-1,3,4-thiadiazin-2-amine, 5-(2,4-dichlorophenyl)-N-methyl-6H-1,3,4-thiadiazin-2-amine, 5-(2,4-dichlorophenyl)-N-ethyl-6H-1,3,4-thiadiazin-2-amine, 5-(2,4-dichlorophenyl)-N,N-dimethyl-6H-1,3,4-thiadiazin-2-amine, 5-(2,4-dichlorophenyl)-N-phenyl-6H-1,3,4-thiadiazin-2-amine, 5-(2,4-dichlorophenyl)-N-(1-methylethyl)-6H-1,3,4-thiadiazin-2-amine, 5-(2,4-dichlorophenyl)-N-propyl-6H-1,3,4-thiadiazin-2-amine, 5-(2-fluorophenyl)-N-methyl-6H-1,3,4-thiadiazin-2-amine, N-ethyl-6-methyl-5-phenyl-6H-1,3,4-thiadiazin-2-amine, 5-(2,4-dichlorophenyl)-N-hexyl-6H-1,3,4-thiadiazin-2-amine and N-butyl-5-(2,4-dichlorophenyl)-6H-1,3,4-thiadiazin-2-amine, 5-(2,4-dichlorophenyl)-N-2-propenyl-6H-1,3,4-thiadiazin-2-amine, 5-(2,4-dichlorophenyl)-N-heptyl-6H-1,3,4-thiadiazin-2-amine and their acid addition salts.

The compounds of this invention are useful as muscle relaxants. These compounds can be administered to warm-blooded animals, mammals, rats, mice, dogs, cats, horses, pigs, cows, sheep and humans. As used herein, the term "patient" is intended to mean the animal or mammal being treated.

The muscle-relaxing activity of the compounds of this invention may be illustrated by their effectiveness in standard pharmacological screening tests, e.g., by demonstrating an antagonism of decerebrate rigidity in rats; by inhibition of polysynaptic reflexes in the anesthetized cat; and by the mouse Straub tail test.

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules and pills, or liquid solutions, suspensions or emulsions for oral and parenteral administration. The dosage unit administered can be any muscle-relaxing effective amount. The quantity of compound administered can vary over a wide range to provide from about 10 to 100, preferably 10-30, mg/kg of body weight of the patient per day, to achieve the desired effect. Unit doses can contain about 5-500 mg of a compound of Formula I and may be administered, for example, from 1 to 4 times daily.

The compounds of Formula I are prepared by reacting a phenacyl halide of the formula

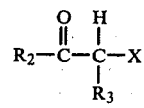

wherein X is Cl or Br, with a 4-substituted thiosemicarbazide of the formula

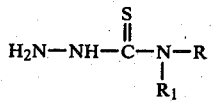

wherein R, $R_1$, $R_2$ and $R_3$ are as hereinbefore defined. The reaction is generally conducted in the presence of a solvent, e.g., a lower alkanol, such as, methanol, ethanol, isopropanol, n-propanol, n-butanol and the like, preferably methanol. The reaction time may vary from about 15 minutes to about 1 hour, preferably about 30 minutes, depending upon the reactants, the solvent and the reaction temperature which may vary from about 60° C. to about 80° C., preferably about 65° C. The product is generally worked-up by permitting the reaction mixture to cool and then concentrating it in vacuo. The resultant residue is recrystallized from an appropriate solvent, e.g., a mixture of a lower alkanol with, e.g., acetone, butanone or ethyl acetate, e.g., methanol/acetone or methanol/ethyl acetate, producing the compound of Formula I as its hydrohalide salt.

Both the phenacyl halide and the 4-substituted thiosemicarbazide which are employed as starting materials in the preparation of the compounds of Formula I are either commercially available or, when unavailable, are very readily preparable by standard chemical reactions which are well-known to those of ordinary skill in the art. For example, the phenacyl halides may be prepared by halogenating the corresponding methyl (optionally-substituted)phenyl ketone using a sulfuryl halide, e.g., sulfuryl chloride, in e.g., acetic acid, to prepare the corresponding phenacyl chloride; or by reacting the corresponding optionally substituted benzene with a haloacetyl halide, e.g., chloroacetyl chloride via a Friedel Crafts reaction using an aluminum trichloride catalyst, e.g., to prepare the corresponding phenacyl chloride. The 4-substituted thiosemicarbazides may be prepared by conventionally reacting the appropriate substituted isothiocyanate with hydrazine in the presence, e.g., of diethyl ether.

EXAMPLES

The following examples are illustrative of the invention.

EXAMPLE 1

N-Methyl-5-phenyl-6H-1,3,4-thiadiazin-2-amine hydrochloride 5.255 g (0.05 mole) of 4-methyl-thiosemicarbazide and 7.73 g (0.05 mole) of phenacyl chloride are heated and stirred at reflux (65° C.) in 200 ml of methanol for 30 minutes. At this time, the solvent is removed in vacuo. The residue is dissolved in methanol, warmed and then diluted with acetone. Thereafter, it is concentrated to approximately 200 ml. After standing for 2 days, 8.33 g of N-methyl-5-phenyl-6H-1,3,4-thiadiazin-2-amine hydrochloride are deposited. m.p. 176°-178° C.

EXAMPLE 2

N-Ethyl-5-(4-fluorophenyl)-6H-1,3,4-thiadiazin-2-amine hydrochloride 11.19 g of 4-ethyl-thiosemicarbazide and 17.6 g of 4-fluorophenacyl chloride are heated and stirred under reflux (65° C.) in 400 ml of methanol for 30 minutes in a one liter round bottom flask equipped with a magnetic stirring bar and a condenser protected by a $CaCl_2$ drying tube. The solution is allowed to cool to room temperature and is then concentrated to a yellow solid residue. The residue is recrystallized from methanol/butanone yielding 21.0 g (75.5%) of N-ethyl-5-(4-fluorophenyl)-6H-1,3,4-thiadiazin-2-amine hydrochloride. m.p. 192°-193° C. The fluffy, yellowish white solid is dried under high vacuum at 65° C.

EXAMPLE 3

5-(2,4-Dichlorophenyl)-6H-1,3,4-thiadiazin-2-amine hydrochloride 11.17 g (0.05 mole) of 2,4-dichlorophenacyl chloride and 4.36 g (0.05 mole) of thiosemicarbazide are stirred and heated in 250 ml of methanol at reflux (65° C.) for 30 minutes. The resultant suspension is allowed to cool and is filtered to yield a first crop of 4.56 g of 5-(2,4-dichlorophenyl)-6H-1,3,4-thiadiazin-2-amine hydrochloride. The reaction mixture is then diluted with ethyl acetate and concentrated on a steam bath further yielding 6.2 g of the same compound. The two products are added together and recrystallized from methanol/ethyl acetate. m.p. 170°-172° C.

EXAMPLE 4

5-(2,4-Dichlorophenyl)-N-methyl-6H-1,3,4-thiadiazin-2-amine monohydrochloride 11.17 g of 2,4-dichlorophenacyl chloride and 5.755 g of 4-methyl-thiosemicarbazide are reacted in 200 ml of methanol using the procedure of Example 2. The initial crystallization is made from methanol/ethyl acetate. The solid is then recrystallized from methanol/ethyl acetate and dried at 65° C. under high vacuum to produce 5-(2,4-dichlorophenyl)-N-methyl-6H-1,3,4-thiadiazin-2-amine monohydrochloride. m.p. 195° C.

EXAMPLE 5

5-(2,4-Dichlorophenyl)-N-ethyl-6H-1,3,4-thiadiazin-2-amine monohydrochloride Utilizing the reaction conditions of Example 2, 9.3 g (0.04 mole) of 2,4-dichlorophenacyl chloride and 4.77 g (0.04 mole) of 4-ethylthiosemicarbazide are reacted in 200 ml of methanol to produce 6.5 g of 5-(2,4-dichlorophenyl)-N-ethyl-6H-1,3,4-thiadiazin-2-amine monohydrochloride after recrystallization which, in this case, was from methanol/ethyl acetate. m.p. 197°-198° C.

EXAMPLE 6

5-(2,4-Dichlorophenyl)-N,N-dimethyl-6H-1,3,4-thiadiazin-2-amine monohydrochloride 4.16 g (0.035 mole) of 4,4-dimethyl-thiosemicarbazide and 7.82 g (0.035 mole) of 2,4-dichlorophenacyl chloride are reacted under the conditions of Example 2. After concentration, ethyl acetate is added to the residue and further concentration is employed. A yellow, needle-like solid is produced. The solid is dried under high vacuum at 65° C. Subsequently, it is recrystallized from methanol/ethyl acetate and again dried under high vacuum to produce 5-(2,4-dichlorophenyl)-N,N-dimethyl-6H-1,3,4-thiadiazin-2-amine monohydrochloride. m.p. 219°-222° C.

EXAMPLE 7

5-(2,4-Dichlorophenyl)-N-phenyl-6H-1,3,4-thiadiazin-2-amine monohydrochloride 4.54 g (0.03 mole) of 4-phenyl-thiosemicarbazide and 6.70 g (0.03 mole) of 2,4-dichlorophenacyl chloride are reacted in 200 ml of methanol using the conditions of Example 2. Recrystallization of the solid is from methanol/ethyl acetate, yielding 6.5 g of 5-(2,4-dichlorophenyl)-N-phenyl-6H-1,3,4-thiadiazin-2-amine monohydrochloride. m.p. 186° C. The solid was subsequently dried under high vacuum at 65° C.

EXAMPLE 8

5-(2,4-Dichlorophenyl)-N-(1-methylethyl-6H-1,3,4-thiadiazin-2-amine monohydrochloride 3.99 g (0.03 mole) of 4-isopropyl-thiosemicarbazide and 6.70 g (0.03 mole) of 2,4-dichlorophenacyl chloride are reacted in 150 ml of methanol under the conditions of Example 2. The concentrated product is crystallized and recrystallized from methanol/ethyl acetate. The product is dried under high vacuum at 65° C. and recrystallized again from methanol/ethyl acetate. It is finally dried again at 65° C. under high vacuum producing 5-(2,4-dichlorophenyl)-N-(1-methylethyl)-6H-1,3,4-thiadiazin-2-amine monohydrochloride. m.p. 207°-208° C.

EXAMPLE 9

5-(2,4-Dichlorophenyl)-N-propyl-6H-1,3,4-thiadiazin-2-amine monohydrochloride 6.70 g (0.03 mole) of 2,4-dichlorophenacyl chloride and 3.99 g (0.03 mole) of 4-n-propyl-thiosemicarbazide are reacted in 150 ml of methanol under the conditions of Example 2. The concentrated product is crystallized and then recrystallized from methanol/ethyl acetate, to produce 6.4 g of 5-(2,4-dichlorophenyl)-N-propyl-6H-1,3,4-thiadiazin-2-amine monohydrochloride. m.p. 184°-185° C. The product is then dried at 65° C. under high vacuum.

EXAMPLE 10

5-(2-Fluorophenyl)-N-methyl-6H-1,3,4-thiadiazin-2-amine monohydrochloride 8.62 g (0.05 mole) of 2-fluorophenacyl chloride and 5.22 g of 4-methyl-thiosemicarbazide are reacted in 150 ml of methanol under the conditions of Example 2. The product is recrystallized from methanol/ethyl acetate, yielding 6.7 g of 5-(2-fluorophenyl)-N-methyl-6H-1,3,4- thiadiazin-2-amine monohydrochloride. m.p. 183°–184° C.

EXAMPLE 11

5-(2,4-Dichlorophenyl)-N-hexyl-6H-1,3,4-thiadiazin-2-amine monohydrochloride 3.50 g of n-hexyl-thiosemicarbazide and 4.47 g of 2,4-dichlorophenacyl chloride are reacted under the conditions of Example 2 in 200 ml of methanol. The resultant solid is recrystallized from methanol/ethyl acetate producing 4.5 g of 5-(2,4-dichlorophenyl)-N-hexyl-6H-1,3,4-thiadiazin-2-amine monohydrochloride. m.p. 173°–174° C.

EXAMPLE 12

N-Butyl-5-(2,4-dichlorophenyl)-6H-1,3,4-thiadiazin-2-amine monohydrochloride 4.47 g of 2,4-dichlorophenacyl chloride and 2.66 g of 4-n-butyl-thiosemicarbazide are reacted under the conditions of Example 2 in 150 ml of methanol. The solid obtained is recrystallized from methanol/ethyl acetate, producing 3.98 g of N-butyl-5-(2,4-dichlorophenyl)-6H-1,3,4-thiadiazin-2-amine monohydrochloride. m.p. 180°–182° C.

EXAMPLE 13

5-(2,4-Dichlorophenyl)-N-2-propenyl-6H-1,3,4-thiadiazin-2-amine monohydrochloride 3.93 g (0.03 mole) of 4-allyl-thiosemicarbazide and 7.00 g (0.03 mole) of 2,4-dichlorophenacyl chloride are reacted in accordance with the conditions of Example 1. Recrystallization from methanol/methyl acetate produces 8 g of 5-(2,4-dichlorophenyl)-N-2-propenyl-6H-1,3,4-thiadiazin-2-amine. m.p. 188°–189° C.

EXAMPLE 14

5-(2,4-Dichlorophenyl)-N-heptyl-6H-1,3,4-thiadiazin-2-amine monohydrochloride 3.78 g (0.02 mole) of 4-n-heptyl-thiosemicarbazide and 4.67 g (0.02 mole) of 2,4-dichlorophenacyl chloride are reacted analogously to Example 1. After recrystallization from methanol/methyl acetate, 5.2 g of 5-(2,4-dichlorophenyl)-N-heptyl-6H-1,3,4-thiadiazin-2-amine monohydrochloride are produced. m.p. 175°–177° C.

EXAMPLE 15

N-Ethyl-6-methyl-5-phenyl-6H-1,3,4-thiadiazin-2-amine hydrobromide 0.05 Mole of -methyl-penacyl bromide and 0.05 mole of 4-ethyl-thiosemicarbazide are reacted using the procedure of Example 1 to prepare 8.0 g of N-ethyl-6-methyl-5-phenyl-6H-1,3,4-thiadiazin-2-amine hydrobromide. m.p. 174°–175° C. After recrystallization from methanol/ethyl acetate, the product is dried at 65° C. under high vacuum.

EXAMPLE 16

5-(4-Fluorophenyl)-N-methyl-6H-1,3,4-thiadiazin-2-amine hydrochloride 8.63 g of 4-fluorophenacyl chloride and 4.66 g of 4-methyl-thiosemicarbazide are reacted by using the conditions of Example 1. The resultant product is recrystallized from methanol/ethyl acetate yielding 5.6 g of 5-(4-fluorophenyl)-N-methyl-6H-1,3,4-thiadiazin-2-amine hydrochloride. M.p. 139°–141° C. The product compound is dried under high vacuum at 65° C.

EXAMPLE 17

An illustrative composition for tablets is as follows:

|  | Per Tablet |
|---|---|
| (a) 5-(2,4-Dichlorophenyl)-N-methyl-6H-1,3,4-thiadiazin-2-amine monohydrochloride | 100.0 mg |
| (b) Wheat starch | 15.0 mg |
| (c) Lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 18

An illustrative composition for a parenteral injection is the following wherein the quantities are on a weight to volume basis.

|  | Amount |
|---|---|
| (a) 5-(2,4-Dichlorophenyl)-N-methyl-6H-1,3,4-thiadiazin-2-amine monohydrochloride | 100.0 mg |
| (b) Sodium chloride | q.s. |
| (c) Water for injection to make | 20.0 ml |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 19

An illustrative composition for hard gelatin capsules is as follows:

|  | Amount |
|---|---|
| (a) 5-(2,4-Dichlorophenyl)-N-methyl-6H-1,3,4-thiadiazin-2-amine monohydrochloride | 200.0 mg |
| (b) Talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 20

An illustrative composition for pills is the following:

|  | Per Pill |
|---|---|
| (a) 5-(2,4-Dichlorophenyl)-N-methyl-6H-1,3,4-thiadiazin-2-amine monohydrochloride | 200 mg |
| (b) Corn Starch | 130 mg |
| (c) Liquid glucose | 20 ml |

The pills are prepared by blending the active ingredient (a) and the corn starch; then adding the liquid glucose with thorough kneading to form a plastic mass from which the pills are cut and formed.

EXAMPLE 21

Compositions similar to those described in Examples 17–20 are prepared except that 5-(4-fluorophenyl)-N-methyl-6H-1,3,4-thiadiazin-2-amine hydrochloride or N-ethyl-5-(4-fluorophenyl)-6H-1,3,4-thiadiazin-2-amine hydrochloride are used in place of the 5-(2,4-dichlorophenyl)-N-methyl-6H-1,3,4-thiadiazin-2-amine hydrochloride.

EXAMPLE 22

The compounds of the preceding examples each can be administered to achieve muscle relaxation in a patient in which a muscle-relaxing effect is desired, e.g., in a patient suffering from a muscle spasm. Muscle relaxation is inducible in rats by administration of chlordiazepoxide (Librium) parenterally (i.v.) So also, the compounds of this invention induce comparable muscle relaxation under similar conditions. For example, the compound of Example 6 has about 3 times the potency of chlordiazepoxide while the compound of Example 10 has about ½ the potency of chlordiazepoxide, under similar conditions of parenteral administration. It is, therefore, anticipated that the compound under consideration will be administered to humans for the same indications and under the same dosage conditions (adjusted for differential potency) as those seen in rats for chlordiazepoxide. For example, the compound of Example 6 could be administered in doses of 1–50 mg. 2 to 4 times daily, to achieve beneficial effects.

What is claimed is:

1. A method of achieving a muscle-relaxing effect in a patient which comprises administering to patient in which a muscle relaxing effect is desired an amount effective to achieve a muscle-relaxing effect of a compound of the formula

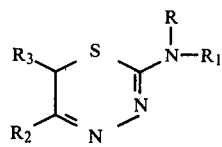

wherein
R is H, or $C_{1-7}$ straight or branched chain alkyl;
$R_1$ is H, $C_{1-7}$ straight or branched chain alkyl, allyl or phenyl;
$R_2$ is phenyl, phenyl monosubstituted with F, Cl, $C_{1-4}$ straight or branched chain alkyl or phenyl disubstituted in the 2- and 4-positions with Cl or $C_{1-4}$ straight or branched chain alkyl; and
$R_3$ is H or $C_{1-4}$ straight or branched chain alkyl, with the proviso that when $R_3$ is straight or branched chain alkyl, $R_2$ is unsubstituted phenyl;
or a pharmaceutically acceptable acid addition salt thereof.

2. The method of claim 1, wherein the amount of the compound administered is 10–100 mg/kg of body weight of the patient per day.

3. The method of claim 1, wherein $R_2$ in the compound administered is substituted phenyl.

4. The method of claim 3, wherein $R_2$ is 2,4-dichlorophenyl.

5. The method of claim 1, wherein the compound administered is 5-(2,4-dichlorophenyl)-N,N-dimethyl-6H-1,3,4-thiadiazin-2-amine monohydrochloride.

6. The method of claim 1, wherein the compound administered is 5-(2,4-dichlorophenyl)-N-2-propenyl-6H-1,3,4-thiadiazin-2-amine.

7. The method of claim 1, wherein the compound administered is 5-(4-fluorophenyl)-N-methyl-6H-1,3,4-thiadizin-2-amine.

8. The method of claim 1, wherein the compound administered is N-ethyl-5-(4-fluorophenyl)-6H-1,3,4-thiadiazin-2-amine.

* * * * *